(12) United States Patent
Suzuki et al.

(10) Patent No.: US 7,258,440 B2
(45) Date of Patent: Aug. 21, 2007

(54) OPHTHALMIC PHOTOGRAPHIC APPARATUS

(75) Inventors: Takayoshi Suzuki, Hamamatsu (JP); Masaharu Mizuochi, Hamamatsu (JP); Kazunori Matsumura, Hamamatsu (JP)

(73) Assignee: Kowa Company Ltd. (JP)

( * ) Notice: Subject to any disclaimer, the term of this patent is extended or adjusted under 35 U.S.C. 154(b) by 674 days.

(21) Appl. No.: 10/823,108

(22) Filed: Apr. 13, 2004

(65) Prior Publication Data

US 2004/0263781 A1 Dec. 30, 2004

(30) Foreign Application Priority Data

Apr. 15, 2003 (JP) .............................. 2003-109691

(51) Int. Cl.
*A61B 3/14* (2006.01)
*A61B 3/10* (2006.01)

(52) U.S. Cl. ..................... 351/206; 351/221; 354/62

(58) Field of Classification Search ................ 351/206, 351/221, 205, 209, 208, 210, 214; 354/62
See application file for complete search history.

(56) References Cited

U.S. PATENT DOCUMENTS 6,325,511 B1 * 12/2001 Mizuochi .................... 351/206

* cited by examiner

*Primary Examiner*—Hung Xuan Dang
(74) *Attorney, Agent, or Firm*—Adams & Wilks

(57) ABSTRACT

An ophthalmic photographic apparatus includes an illumination optical system for illuminating an eye fundus and a photographing optical system for photographing an image of the illuminated eye fundus. The ophthalmic photographic apparatus includes a first aperture stop, a second aperture stop having an outside diameter that is smaller than that of the first aperture stop, a third aperture stop that transmits more light than the first aperture stop, and means for selectively inserting the first to third aperture stops into the optical path of the illumination optical system. The ophthalmic photographic apparatus does not have a complicated structure, but can be readily used in the various photographing modes.

16 Claims, 6 Drawing Sheets

FIG. 3

| Ring Slit | Exciter | Barrier | Observation & Photography Light Amount | Photographic Mode | Timer | Observation Mode | Photographic Means |
|---|---|---|---|---|---|---|---|
| Standard 11 | No | No | 0 | Mydriatic | No | Finder or Infrared CCD | (Still Images) Color CCD or 35mm |
| | FA | FA | +3 | FA | T1 | Finder or Infrared CCD | ✕ |
| | ICG | No | +6 | ICG | T2 | Infrared CCD | |
| Small Pupil 12 | No | No | +1 | Non-Mydriatic | No | Infrared CCD | |
| | | | | Mydriatic | No | Finder or Infrared CCD | (Still Images) Color CCD or 35mm |
| | FA | FA | +4 | FA | T1 | Finder or Infrared CCD | |
| | ICG | ICG | +5 | ICG | T2 | Infrared CCD | (Still or Moving Images) Infrared CCD |
| Fluorescence 13 | FA | FA | +2 | FA | T1 | Finder or Infrared CCD | (Still Images) Color CCD or 35mm |

OPHTHALMIC PHOTOGRAPHIC APPARATUS

BACKGROUND OF THE INVENTION

1. Field of the Invention

The present invention relates to an ophthalmic photographic apparatus, and more particularly to an ophthalmic photographic apparatus that includes an illumination optical system for projecting illuminating light onto a subject eye fundus via an aperture stop such as a ring slit or the like, and a photographing optical system that photographs the fundus thus illuminated.

2. Description of the Prior Art

There are various ways of photographing the eye fundus in color using an ophthalmic photographic apparatus such as a fundus camera. In mydriatic photography, a mydriatic agent is administered to the eye, which is taxing for the patient. There is also non-mydriatic photography in which a mydriatic agent is not used. In non-mydriatic photography, infrared light is projected onto the fundus and the fundus is photographed after the alignment is completed. There is also fluorescent photography, which includes fluorescein angiography for photographing visible fluorescent images, and ICG (indocyanine green) fluorophotography (ICG angiography) for photographing infrared fluorescent images. Each photography mode uses different illumination and photographing filters, and the optical characteristics also differ. It is, therefore, preferable to use a specialized fundus camera for each mode. However, from the standpoint of cost-performance, fundus cameras are being developed that can be used for various modes. For example, Japanese Laid open Patent Publication No. Hei9-140672 describes a fundus camera that can be used for mydriatic and non-mydriatic photography and fluorescein angiography; Japanese Laid open Patent Publication No. Hei 8-150120 describes a fundus camera that can be used for mydriatic photography (color), fluorescein angiography and ICG fluorophotography; Japanese Laid open Patent Publication No. Hei 1-300926 also describes a fundus camera that can be used for mydriatic photography (color), fluorescein angiography and ICG fluorophotography; and Japanese Patent No. 2894359 describes mechanisms for interlocking variable power lenses, fluorescent filters and ring slits depending upon the photographing modes.

However, for a fundus camera to be able to handle mydriatic, non-mydriatic, fluorescein angiographic and ICG fluorophotographic modes, it has to be able to insert complex combinations of filters into the optical path and retract the filters from the optical path when the system is switched among the four modes. This increases the complexity of the apparatus and of the various setting operations, increasing the misoperations. For these reasons, there is no fundus camera that can handle the above four photographing modes.

SUMMARY OF THE INVENTION

An object of this invention is therefore to provide an ophthalmic photographic apparatus that, using a simple structure, can photograph the eye fundus in at least the mydriatic, non-mydriatic, fluorescein angiographic and ICG fluorophotograpic modes.

To attain this object, the invention provides an ophthalmic photographic apparatus that includes an illumination optical system for illuminating an eye fundus and a photographing optical system for photographing an image of the illuminated eye fundus. The ophthalmic photographic apparatus according to the invention includes a first aperture stop, a second aperture stop having an outside diameter that is smaller than that of the first aperture stop, a third aperture stop that transmits more light than the first aperture stop, and means for selectively inserting the first to third aperture stops into an optical path of the illumination optical system.

The third aperture stop is provided with wavelength characteristics so that it transmits only light in the infrared region.

In accordance with this invention, ring slits and illumination filters are used in common for the different photographing modes, making it possible to provide the ophthalmic photographic apparatus with good usability in each photographing mode and provide with a non-complex structure because a low number of optical elements are employed.

Further features of the invention, its nature and various advantages will be more apparent from the accompanying drawings and following detailed description of the invention.

BRIEF DESCRIPTION OF THE DRAWINGS

FIG. 3 is a table showing ring slit and filter usage in each photographing mode, categories of observation and photographing means, and other details;

DESCRIPTION OF THE PREFERRED EMBODIMENTS

Preferred embodiments of the present invention will now be described with reference to the drawings.

Figure 1:
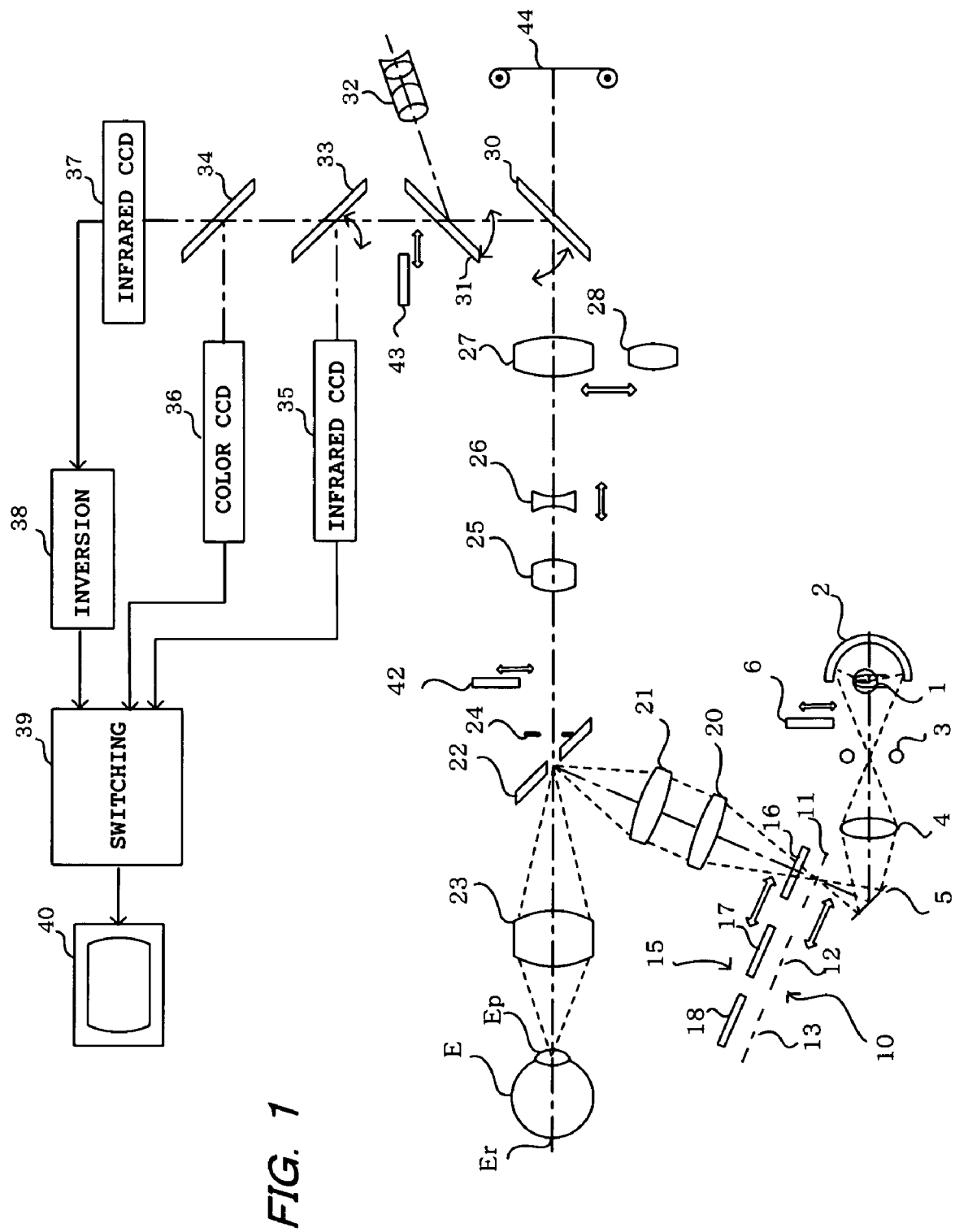
FIG. 1 is a view showing the arrangement of an ophthalmic photographic apparatus according to a first embodiment of the invention.

FIG. 1 is a drawing of the ophthalmic photographic apparatus (fundus camera) of this invention. Light from an observation light source 1 such as a halogen lamp or the like is concentrated by a concave mirror 2. The light then passes a strobe 3, which constitutes a photographing light source, passes through a condenser lens 4, is reflected by a mirror 5, is relayed by relay lenses 20 and 21 and is reflected by a total reflection mirror 22 having an aperture. The light thus reflected is collected at the pupil Ep of the eye by an objective lens 23 and projected onto the fundus Er of an eye E to be examined.

Figure 2A:
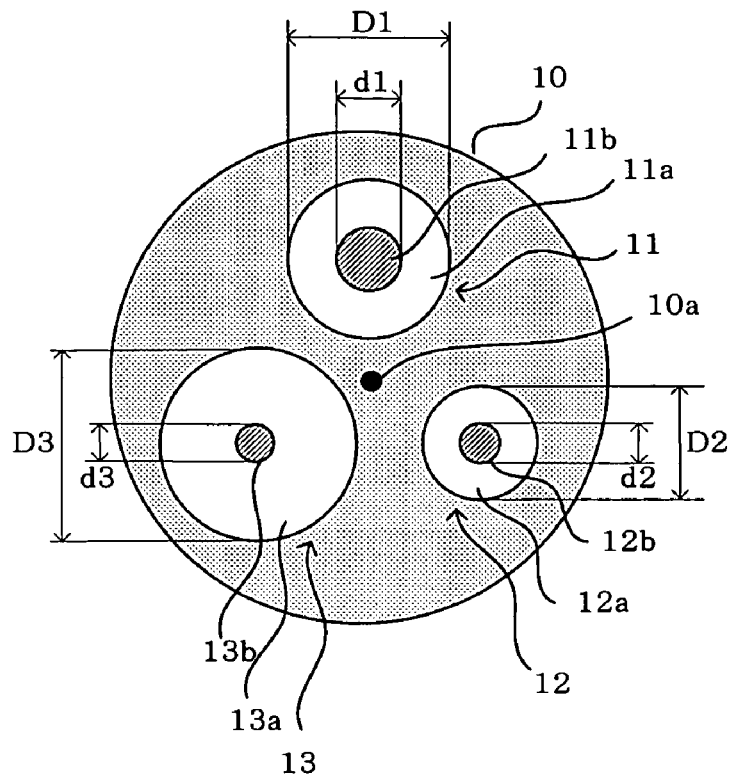
FIG. 2a is a front view of the turret arrangement used to switch ring slits.

During non-mydriatic operation, an infrared transmission filter 6 is inserted in front of the light source 1 into the optical path of the illumination optical system. The illumination system has a turret 10, which can switch among a plurality of ring slits 11 to 13, and a turret 15, which can switch among a plurality of illumination filters 16 to 18. As shown in FIG. 2a, the turret 10 can rotate about an axis 10a around which are arrayed a standard ring slit (first ring slit) 11, a small-pupil ring slit (second ring slit) 12 and a large fluorescent ring slit (third ring slit) 13. Any of these ring slits can be inserted into the optical path so that the center of the slit is in alignment with the optical axis of the illumination system.

The standard ring slit 11 is composed of an annular aperture 11a and a round shield plate 11b, which are concentrically arranged with the outside diameter D1 of the ring slit 11 (the diameter of the annular aperture 11a) and the inside diameter d1 of the ring slit 11 (the diameter of the shield plate 11b). The small-pupil ring slit 12 is composed of an annular aperture 12a and a round shield plate 12b, which are concentrically arranged with the outside diameter D2 of the ring slit 12 (the diameter of the annular aperture 12a) being smaller than the outside diameter D1 of the standard ring slit 11 and with the inside diameter d2 thereof (the diameter of the shield plate 12b) being smaller than the inside diameter d1 of the standard ring slit 11. The fluorescent ring slit 13 is composed of an annular aperture 13a and a round shield plate 13b, which are concentrically arranged with the outside diameter D3 of the ring slit 13 (the diameter of the annular aperture 13a) being larger than the outside diameter D1 of the standard ring slit 11 and with the inside diameter d3 thereof (the diameter of the shield plate 13b) being smaller than the inside diameter d1 of the standard ring slit 11.

With this configuration, the small-pupil ring slit 12 has at least a smaller outside diameter than the standard ring slit 11. On the other hand, the area of the portion of the fluorescent ring slit 13 that transmits illuminating light is larger than that of the standard ring slit 11. The amount of light that is thus transmitted is correspondingly larger.

The image of each of these ring slits inserted into the optical path of the illumination system is formed substantially at the position of the pupil Ep of the eye E, and the fundus is evenly illuminated by light passing through the ring slit. Harmful light reflecting from the fundus at this time is blocked by the image of the shield plate of each slit. The small-pupil ring slit 12 is used in small-pupil situations such as when the eye is not sufficiently dilated, or when the patient is a child. In addition to having a smaller outside diameter than the standard ring slit 11, the ring slit 12 also has a smaller inside diameter to prevent the amount of illuminating light from being decreased. The ring slit 13 is used mainly during ICG fluorophotography. To maximize the amount of incident illuminating light, the ring slit 13 has been given an outside diameter that is larger than that of the standard ring slit 11, and an inside diameter that is smaller. Normally the standard ring slit 11 is used during fluorescein angiography, but if more light is required, the ring slit 13 with its large slit can be used.

Figure 2B:
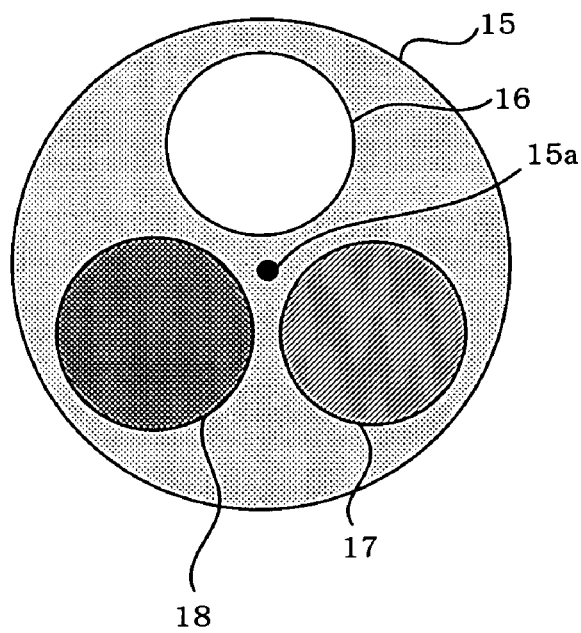
FIG. 2b is a front view of the turret arrangement used to switch illumination filters.

The turret 15 is positioned behind the turret 10. The turret 15 can rotate about the axis 15a, and as shown in FIG. 2b, has a through-filter 16, an exciter filter 17 for fluorescein angiography that transmits blue-green light having a wavelength of 450 nm to 520 nm, and an exciter filter 18 for ICG fluorophotography that transmits infrared light having a wavelength of 700 nm to 800 nm. Any filter can be inserted into the illumination optical path by rotating the turret 15. The through-filter 16 can be used to transmit all of the light. The exciter filter 17 is used for fluorescein angiography. The exciter filter 18 is used for ICG fluorophotography to transmit only infrared light.

Light reflected by the fundus Er passes back through the center of the pupil Ep and the objective lens 23, the aperture of the total reflection mirror 22, photographic aperture stop 24, focusing lenses 25 and 26 and imaging lens 27 disposed on the photographic optical path, and falls incident on a first return mirror 30. The imaging lens 27 can be exchanged with the imaging lens 28 having a different magnification, thereby forming a variable power mechanism. During fluorescein angiography, a barrier filter 42 can be inserted between the photographing stop 24 and the focusing lens 25 to transmit visible fluorescence from the eye fundus.

Light from the fundus reflected by the return mirror 30 is reflected by a second return mirror 31 to fall incident on a finder 32 constituting a naked-eye observation optical system, making it possible for an eye examiner to view the fundus image via the finder 32. By inserting the infrared transmission filter 6 into the optical path and retracting the return mirror 31 from the optical path, the light from the fundus can be reflected by a third return mirror 33 to fall incident on an optical system used for viewing by infrared light. An infrared image of the fundus produced by the infrared observation system in which an imaging unit 35 in the form of an infrared CCD is employed is displayed on a monitor 40 via a switching circuit 39. The imaging unit 35 images the fundus during observation, so that the examiner can align and focus the system while viewing infrared moving images of the fundus.

During ICG fluorophotography (ICG angiography), an ICG fluorophotographic barrier filter 43 that transmits infrared light having a wavelength of from 820 nm to 900 nm can be inserted into the optical path between the return mirrors 31 and 33.

When the return mirror 33 is retracted from the optical path, light from the fundus falls incident on a dichroic mirror 34, which separates the visible light from the infrared light. Visible light reflected by the dichroic mirror 34 falls incident on an imager constituted by a color CCD 36 that is sensitive to visible light. Infrared light transmitted by the dichroic mirror 34 falls incident on an imager constituted by an infrared CCD 37 that is sensitive to infrared light. The fundus image produced by the color CCD 36 is the image reflected by the dichroic mirror 34, so that it is an inversion of the image obtained by the infrared CCD 37. Therefore, by providing and using an image inversion circuit 38, either of the images from the color CCD 36 and infrared CCD 37 can be subjected to inversion processing to vertically align observation and photographic images. Fundus images produced by the imaging units 36 and 37 using light emitted by the photographing strobe 3 are displayed via the switching circuit 39 on the monitor 40 as still fundus images. Although not shown, the system of FIG. 1 is provided with a recording apparatus to record fundus images produced by the imaging units 36 and 37.

When the return mirror 30 is retracted from the optical path, fundus images can be recorded on photographic film 44 such as 35 mm film. Instead of photographic film, fundus images can be also recorded using an imaging unit equivalent to the color CCD 36.

The ophthalmic photographic apparatus thus constituted can operate mydriatic mode, non-mydriatic mode, fluorescein angiographic mode and ICG fluorophotographic mode. Ordinary color photography is carried out in mydriatic or non-mydriatic mode.

In the mydriatic photography mode, a mydriatic agent is administered to the patient. During this time, the infrared transmission filter 6 is retracted from the optical path. Normally, the standard ring slit 11 is used, but in cases where the pupil is small, the small-pupil ring slit 12 is used. The through-filter 16 is inserted into the optical path. Since the barrier filters 42 and 43 are for fluorescent photography, they are retracted from the optical path. Return mirrors 30, 31 and 33 occupy the positions shown in FIG. 1. Light from the observation light source 1 is reflected by the mirror 5 and passes through the standard ring slit 11 (or the small-pupil ring slit 12), the through-filter 16 and the relay lenses 20 and 21, and is reflected onto the objective lens 23 by the total reflection mirror 22, whereby the eye fundus Er is illuminated. Reflected light from the fundus Er passes back through the objective lens 23, the total reflection mirror 22, the photographic aperture stop 24, the focusing lenses 25 and 26 and the imaging lens 27, and is deflected onto the finder 32 by the return mirrors 30 and 31. This enables the examiner to view the fundus and align the system and adjust the focus and so forth. When the alignment and adjustments have been completed, the examiner presses the shutter button (not shown) to operate the shutter. This also causes the strobe 3 to operate and the return mirror 30 to be retracted from the optical path, making it possible to obtain a color photograph on the film 44 (or on a color CCD) or the like. Infrared viewing of the fundus is possible without using the finder 32, in which case the return mirror 31 is retracted from the optical path and moving images of the fundus are obtained via the infrared imaging unit 35. The fundus images can be displayed on the monitor 40 by using the switching circuit 39, so that the examiner can carry out system alignment and focusing while viewing the fundus images on the monitor 40.

FIG. 3 shows an outline of system settings. In the mydriatic photography mode, the standard or small-pupil ring slit is selected depending on whether the size of the pupil is standard or small. The through-filter is used, so that no exciter filter is used, as indicated by the "No". The barrier filters 42 and 43 are both retracted from the optical path, again as indicated by "No". The amount of observation and photography light is set according to the ring slit selected. In the case of the standard ring slit, the setting is "0" (the default), and "+1" in the case of the small-pupil ring slit. In fluorescent photographic modes, the timer (not shown) is used to measure the time elapsed from the intravenous injection of the fluorescence agent. When fluorescent photography is not being used, the timer is not used, as indicated in this case by the "No". The fundus can be viewed by the naked eye via the finder 32, or by the infrared CCD 35 images displayed on the monitor 40. The images can be photographed using 35 mm film or a color CCD.

In the non-mydriatic photography mode, the infrared transmission filter 6 is inserted into the optical path and the small-pupil ring slit 12 is selected. The return mirror 31 is retracted from the optical path and, unlike in the case of the mydriatic mode, observation is done using images obtained by the infrared imaging unit 35 which are displayed on the monitor 40. Hence, in FIG. 3, "Infrared CCD" is listed as the observation means. The photography setting is the same as that used in mydriatic photography. In the non-mydriatic photography mode, there is no administration of a mydriatic agent, which is less burdening the patient.

In fluorescein angiographic mode, the standard ring slit 11 or small-pupil ring slit 12 is selected depending on whether the size of the pupil is standard or small. The exciter filter 17 is selected as the illuminating light filter and the barrier filter 42 is selected as the photographic filter. When the monitor is being used to observe the images from the infrared CCD 35, the infrared transmission filter 6 is inserted into the optical path and the return mirror 31 is retracted from the optical path. When the finder 32 is being used for observation, the infrared transmission filter 6 is retracted from, and the return mirror 31 is inserted into the optical path. During observation via the finder 32, the exciter filter 17 is inserted into the optical path. When system alignment and focusing have been completed, the fluorescent agent is intravenously injected, the exciter filter 17 and barrier filter 42 are inserted into the optical path and the timer starts measuring the elapsed time. After the passage of a prescribed time T1, a visible fluorescent image is produced on the fundus by exciting light passing through the exciter filter 17. At this time, the shutter button is depressed to operate the shutter, triggering the strobe 3. At this instant the return mirror 30 is retracted, so that the images are recorded using 35 mm film or a color CCD. The same operation takes place each time the shutter is operated. When color CCD 36 is used to obtain color images, the return mirror 30 is inserted into the optical path, and the return mirrors 31 and 33 are retracted therefrom. Since light from the light source 1 becomes a hindrance when the color CCD 36 is used, it is preferable to turn off the light source 1. However, the ICG fluorophotographic barrier filter 43 blocks visible light, so that, instead of turning the light source 1 off, the barrier filter 43 can be inserted into, or retracted from the optical path in accordance with the image data storage time of the color CCD 36. Depending on the condition of the eye, instead of the standard ring slit 11, the fluorescent ring slit 13 can be used to provide more illumination in the fluorescein angiographic mode.

FIG. 3 shows an outline of system settings in the fluorescein angiographci mode (designated by FA). When the small-pupil ring slit 12 is used, the observation and photography light amount can be increased if required. For example, to increase the amount of light when the standard ring slit setting is "+3", a setting of "+4" is used when the small-pupil ring slit is selected. The amount of observation and photography light is decreased when the fluorescent ring slit 13 is used because it can cause a large amount of light to be projected onto the eye. This is indicated in FIG. 3 by the "+2".

During ICG fluorophotography, increasing the amount of illumination and photography light is not more taxing for the patient, and there is also a decrease in sensitivity. Therefore, the fluorescent ring slit 13 is selected to increase the amount of observation and photography light and maximize the amount of light projected onto the fundus. The exciter filter 18 is used as the illumination filter and the barrier filter 43 is used as the photographing filter. During observation, the large ring slit 13 (or standard ring slit 11) and the exciter filter 18 are inserted into the optical path and the return mirror 31 is retracted from the optical path, allowing images obtained by the infrared CCD 35 to be displayed on the monitor. When system alignment and focusing have been completed, the ICG is intravenously injected, the barrier filter 43 is inserted into the optical path and the timer is started. After a prescribed time T2 has elapsed, an infrared fluorescence image is produced on the fundus by exciting light passing through the exciter filter 18. At this time, the shutter button is depressed to operate the shutter, activating the strobe 3. In this case, the return mirror 30 is fixed in the illustrated position and the return mirror 31 is fixed in the retracted position. Each time the shutter is operated, the return mirror 33 is retracted, whereby the infrared fluorescent image is transmitted by the dichroic mirror 34 and imaged by the infrared CCD 37. This infrared fluorescent image is vertically inverted by image inversion circuit 38 and, via the switching circuit 39, is displayed on the monitor 40 as a still image.

In the case of ICG fluorophotographic mode, as shown in FIG. 3, the fluorescent ring slit 13 or the standard ring slit 11 is used and the amount of observation and photography light is adjusted according to the ring slit used. When the fluorescent ring slit is used, for example, the setting is "+5", and "+6" in the case of the standard ring slit.

The fluorescent ring slit 13 is inserted into the optical path mainly during ICG fluorophotography. At those times, the filter inserted into the optical path is the exciter filter 18 which transmits only infrared light. Therefore, instead of selecting the filters by using separate turrets as shown in FIG. 1, the ring slit 13 and exciter filter 18 can be integrated and located on either turret. In this case, the ring slit 13 would only transmit infrared light. This means that it would have the wavelength characteristics of an ICG exciter filter, and a separate ICG exciter filter would no longer be necessary. This simplifies the system structure.

Instead of using the turret 10, the ring slit 13 could be fixed in the optical path and a solenoid or the like is used to selectively slide the standard ring slit 11 or small-pupil ring slit 12 into the optical path depending on the photography mode that is used. In instances in which neither the standard ring slit 11 nor the small-pupil ring slit 12 is selected, the fluorescent ring slit 13 is fixed in the optical path, which is the same as the ring slit 13 being selected by using the turret. As shown in FIG. 2a, the fluorescent ring slit 13 fixed in the optical path has a small inside diameter d3 and a large outside diameter D3, so that the same effect can be obtained as that obtained by turret selection of the standard ring slit 11 and the small-pupil ring slit 12.

Similarly, instead of using the turret 15, a solenoid or the like can be used to selectively slide the fluorescein exciter filter 17 and the ICG exciter filter 18 into the optical path. When neither the exciter filter 17 or the exciter filter 18 is selected, it is the same as the through-filter 16 being selected by the turret. When either filter 17 or 18 is selected, the same effect can be obtained as when the corresponding filter 17 or 18 is selected by the turret.

Figure 4:
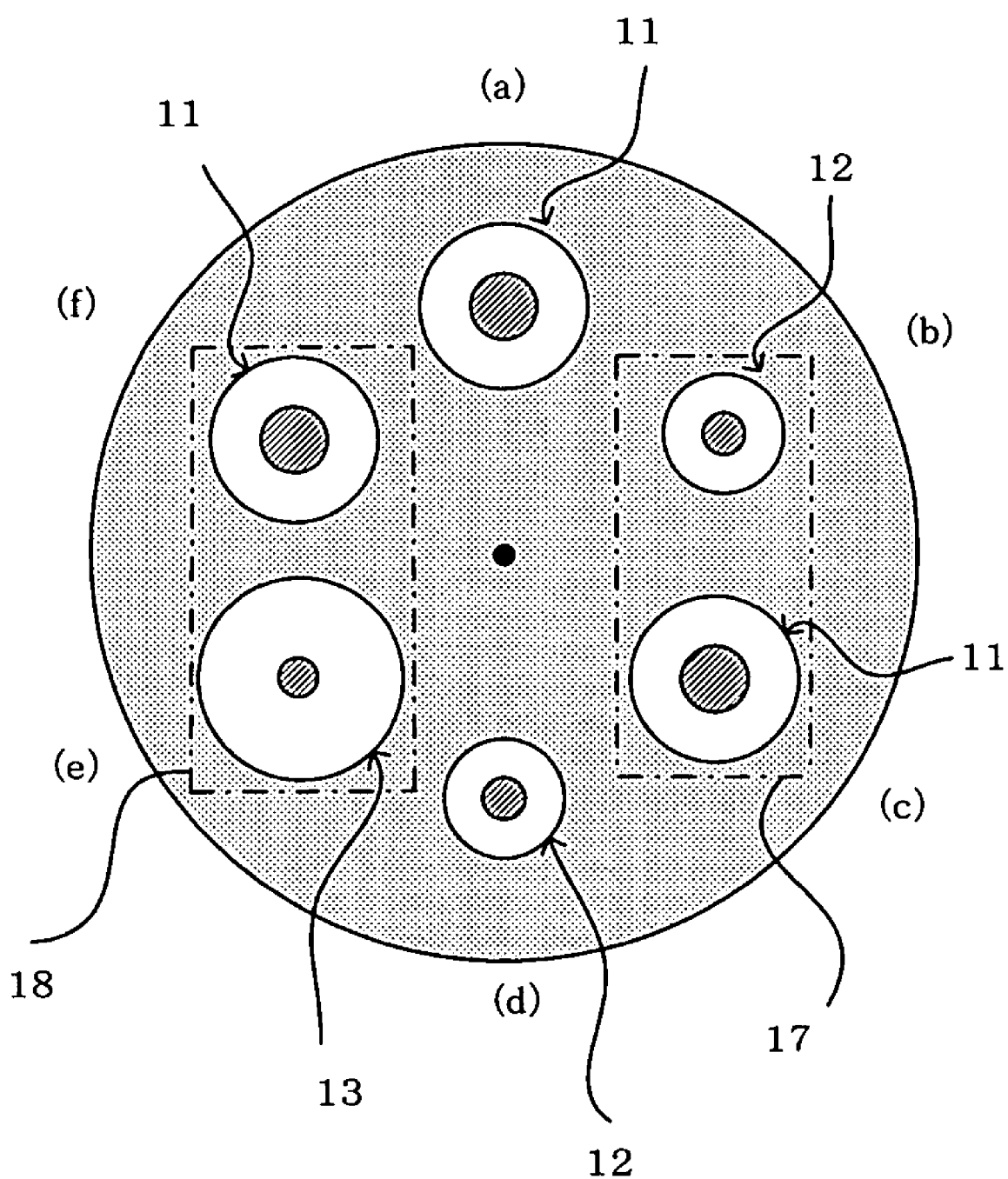
FIG. 4 is a view illustrating another embodiment for switching ring slits and illumination filters.

The ring slits and illumination filters for each photographic mode can be integrated and the two turrets 10 and 15 consolidated. An example of this is shown in FIG. 4. Three standard ring slits 11, two small-pupil ring slits 12 and one fluorescent ring slit 13 are arrayed on a single turret disk. The fluorescein exciter filter 17 is attached to one of the standard ring slits and small-pupil ring slit with the standard ring slit and small-pupil ring slit integrated with the fluorescein exciter filter ((b), (c)). Also, the ICG exciter filter 18 is attached to the other standard ring slit and fluorescent ring slit with the standard ring slit and fluorescent ring slit integrated with the ICG exciter filter ((e), (f)).

With this arrangement, in the case of the topmost mydriatic photography mode of FIG. 3, the standard ring slit at position (a) is selected for insertion into the optical path; in the case of the second fluorescein angiographic mode, the standard ring slit integrated with the fluorescein exciter filter at position (c) is selected; in the case of the third ICG fluorophotographic mode, the standard ring slit integrated with the ICG exciter filter at position (f) is selected; in the case of the fourth non-mydriatic mode and the fifth mydriatic photographic mode, the small-pupil ring slit at position (d) is selected; in the case of the sixth fluorescein angiographic mode, the small-pupil ring slit integrated with the fluorescein exciter filter at position (b) is selected; and in the case of the seventh ICG fluorophotographic mode, the fluorescent ring slit integrated with the ICG exciter filter at position (e) is selected. In this example, the selection mechanism is simplified and usability is improved because the corresponding ring slit and exciter filter are integrated.

Figure 5:
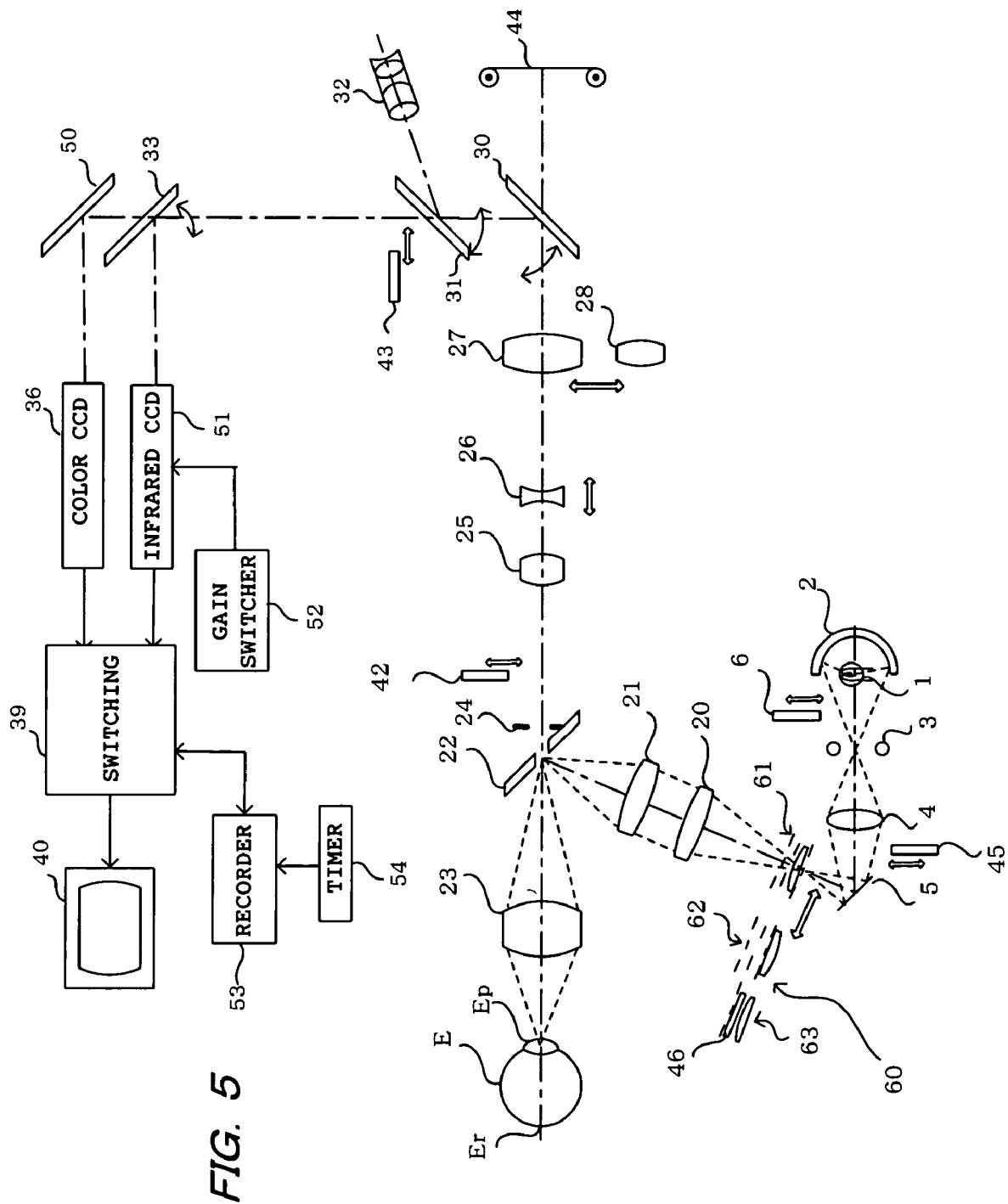
FIG. 5 is a view showing the arrangement of an ophthalmic photographic apparatus according to another embodiment of the invention.

FIG. 5 shows another embodiment of the invention. Compared to the first example, this embodiment has a different ring slit and illumination filter configuration, and the infrared CCD camera is used for both observation and photography. Other parts are the same. Therefore, parts that are the same or similar to those in the embodiment of FIG. 1 have been given the same reference symbols and numbers, and further explanation thereof is omitted.

As in the configuration of FIG. 1, standard ring slit 61, small-pupil ring slit 62 and fluorescent ring slit 63 are disposed on a turret. Any slit can be inserted into the optical path by rotating the turret or by using a sliding mechanism or the like.

Figure 6:
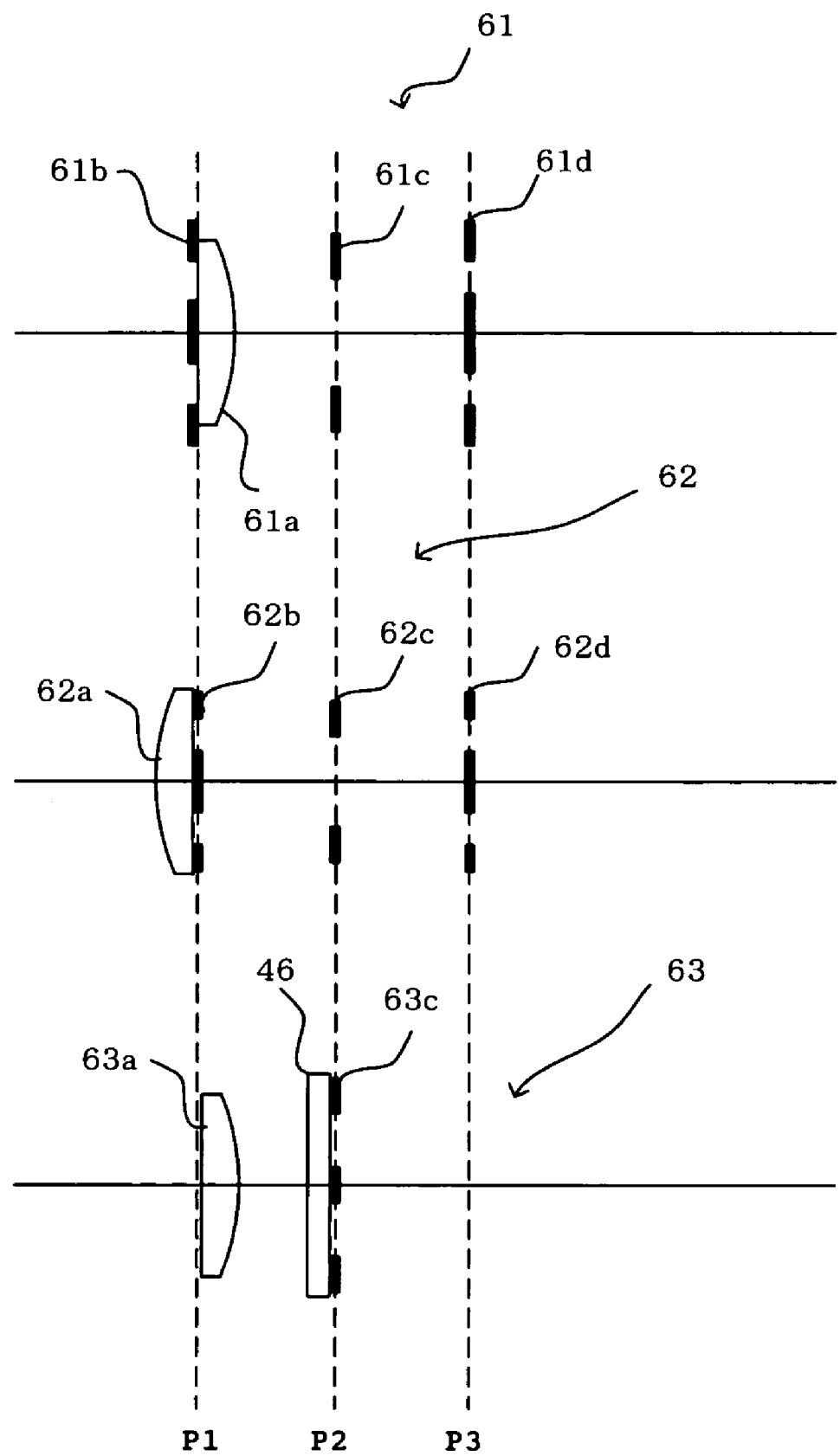
FIG. 6 is a view illustrating details of the ring slit configuration in the apparatus of FIG. 5.

As shown in FIG. 6, each ring slit is composed of a lens and a plurality of aperture stops. The standard ring slit 61 is composed of a lens 61a, a ring slit 61b (having, for example, an outside diameter of 16 mm and an inside diameter of 8 mm), a circular aperture 61c (having a diameter of 12 mm, for example) and a ring slit 61d (having, for example, an outside diameter of 16 mm and an inside diameter of 8 mm). These elements 61a, 61b, 61c and 61d are integrated to form a single unit. The small-pupil ring slit 62 is composed of a lens 62a, a ring slit 62b (having, for example, an outside diameter of 13 mm and an inside diameter of 7 mm), a circular aperture 62c (having a diameter of 10 mm, for example) and a ring slit 62d (having, for example, an outside diameter of 13 mm and an inside diameter of 7 mm). These elements 62a, 62b, 62c and 62d are integrated to form a single unit. The fluorescent ring slit 63 is composed of a lens 63a (having a diameter of 18 mm, for example) and a ring slit 63c (having, for example, an outside diameter of 16 mm and an inside diameter of 2 mm), and is also provided with an ICG exciter filter 46 (corresponding to the exciter filter 18 of the first example shown in FIG. 1). These elements 63a, 63c and 46 are integrated to form a single unit.

The ring slit 61b of the standard ring slit 61 and ring slit 62b of the small-pupil ring slit 62 are each located at a position P1 that is conjugate with the cornea. The lens barrel has a constricting effect, so that the circular aperture is formed at a position P1 in the fluorescent ring slit 63. With respect to the apertures formed at the corneal conjugate position P1, the inside diameter and outside diameter of the ring slit 62b are smaller than the inside diameter and outside diameter of the ring slit 61b. On the other hand, the circular aperture formed in the fluorescent ring slit 63 at position P1 has a diameter that is substantially the same as that of the lens 63a, so that this circular aperture transmits more illuminating light than the ring slit 61b.

The circular apertures 61c and 62c and ring slit 63c are each located at a position P2 that is conjugate with the pupil. The diameter of the circular aperture 62c is smaller than that of the aperture 61c. On the other hand, the ring slit 63c transmits more illuminating light than the circular aperture 61c.

The ring slits 61d and 62d are each located at a position P3 that is conjugate with the crystalline lens. A circular aperture in the fluorescent ring slit 63 is formed at a position P3 because the lens barrel has a constricting effect and provides an aperture. With respect to the apertures formed at the crystalline lens conjugate position P3, the outside diameter and inside diameter of the ring slit 62d are smaller than the outside diameter and inside diameter of the ring slit 61d, and the circular aperture formed in the fluorescent ring slit 63 at the position P3 has a diameter that is substantially the same as that of the lens 63a, so that this circular aperture transmits more illuminating light than the ring slit 61d.

In the embodiment shown in FIG. 5, the through-filter 16 used in the first example is substituted by the lenses 61a, 62a and 63a. In the embodiment of FIG. 5, the fluorescein exciter filter 17 of FIG. 1 is constituted by a fluorescein exciter filter 45 that is retractably inserted between the lens 4 and the mirror 5, while the ICG exciter filter 18 of FIG. 1, as described above, is integrated into the fluorescent ring slit 63 in the form of the ICG exciter filter 46.

As in the case of the embodiment of FIG. 1, the standard, small-pupil, and fluorescent ring slits 61 to 63 and the fluorescein and ICG exciter filters 45 and 46 are selected to carry out fundus observation and photography according to the table in FIG. 3 in the mydriatic, non-mydriatic, fluorescein angiographic and ICG fluorophotographic modes. The relationships between the illumination apertures and the amount of transmitted light are the same as in the case of the configuration of FIG. 1, so that the same effect can be obtained.

In the photographic optical system in the embodiment of FIG. 5, the observation infrared CCD 35 and photographic infrared CCD 37 of FIG. 1 are integrated into the one infrared CCD 51 unit having both functions. This means the embodiment of FIG. 5 can be built at a lower cost than the embodiment of FIG. 1. When the CCD 51 is changed over between observation and photography, sensitivity of the CCD 51 has to be changed, for which a gain switching circuit 52 is provided. In photography mode, the CCD sensitivity is switched from the observation setting in synchronism with the shutter operation to reduce the photography sensitivity compared to observation sensitivity. On the other hand, the sensitivity of the CCD 51 is increased during observation mode. It is preferable to have an adjustable gain to allow the sensitivity to be adjusted for each photographing mode.

It is also preferable to associate photographic time data with the fundus still image information. For this purpose, a timer 54 is connected to the still-image recording unit 53 to record when fundus photographs are taken.

What is claimed is:

1. An ophthalmic photographic apparatus that includes an illumination optical system for illuminating an eye fundus and a photographing optical system for photographing an image of the illuminated eye fundus, said ophthalmic photographic apparatus comprising:
   a first aperture stop,
   a second aperture stop having an outside diameter that is smaller than that of the first aperture stop,
   a third aperture stop that transmits more light than the first aperture stop, and
   means for selectively inserting the first to third aperture stops into an optical path of the illumination optical system.

2. An ophthalmic photographic apparatus according to claim 1, wherein the third aperture stop has wavelength characteristics of an ICG exciter filter.

3. An ophthalmic photographic apparatus according to claim 2, wherein a photographing filter having wavelength characteristics for transmitting infrared fluorescence is inserted into an optical path of the photographing optical system when the third aperture stop is inserted into the optical path of the illumination optical system.

4. An ophthalmic photographic apparatus according to claim 3, wherein a wavelength region transmitted by the photographing filter differs from a wavelength region transmitted by the third aperture stop.

5. An ophthalmic photographic apparatus according to claim 3, wherein a wavelength region transmitted by the illumination optical filter differs from a wavelength region transmitted by the photographing filter.

6. An ophthalmic photographic apparatus according to claim 1, wherein an illumination optical filter having wavelength characteristics of an ICG exciter filter is inserted into the optical path of the illumination optical system when the third aperture stop is inserted into the optical path of the illumination optical system.

7. An ophthalmic photographic apparatus according to claim 1, further including a first return mirror provided on the optical path of the photographing optical system, a second return mirror provided on the optical path of reflected light from the first return mirror, an observation optical system for naked-eye observation provided on the optical path of reflected light from the second return mirror, a first imaging unit provided on the optical path of transmitted light when the first return mirror is retracted, a third return mirror provided on the optical path of transmitted light when the second return mirror is retracted, an infrared observation and photographing unit provided on the optical path of reflected light from the third return mirror, and a second imaging unit provided on the optical path of transmitted light when the third return mirror is retracted.

8. An ophthalmic photographic apparatus according to claim 7, wherein the second imaging unit comprises an infrared electronic imaging apparatus that receives a separated infrared light beam, and a visible-light electronic imaging apparatus that receives a separated visible light beam.

9. An ophthalmic photographic apparatus according to claim 8, wherein, when the visible-light electronic imaging apparatus is used to take a still image, the photographing filter is inserted into, and removed from, the photographing optical path in accordance with an image data storage time of the visible-light electronic imaging apparatus.

10. An ophthalmic photographic apparatus according to claim 8, wherein either of an image taken by the infrared electronic imaging apparatus or an image taken by the visible-light electronic imaging apparatus is displayed as an inverted image.

11. An ophthalmic photographic apparatus according to claim 7, wherein, when the illumination and photographing filters are inserted into the optical path, the first return mirror is fixed at the inserted position, the second return mirror is fixed at the retracted position, and retraction of the third return mirror takes place as a photography is initiated.

12. An ophthalmic photographic apparatus according to claim 7, wherein, when the illumination optical filter having the wavelength characteristics of the ICG exciter filter and the photographing filter having the wavelength characteristics for transmitting infrared fluorescence are inserted into the optical path, the first return mirror is fixed at the inserted position, the second return mirror is fixed at the retracted position, the third return mirror is fixed at the inserted position, and images of the infrared observation and photography unit are recorded as still image information, said recording operation being interlocked with a photographing operation.

13. An ophthalmic photographic apparatus according to claim 12, wherein a photographing light source emits light in conjunction with a photographing operation.

14. An ophthalmic photographic apparatus according to claim 12, wherein changeover of a sensitivity setting of the infrared observation and photographing unit from an observation setting to a photography setting is interlocked with a photographing operation.

15. An ophthalmic photographic apparatus according to claim 14, wherein the observation setting is adjustable.

16. An ophthalmic photographic apparatus according to claim 12, wherein the still image is recorded together with photographic time information.

\* \* \* \* \*